(12) United States Patent
Michnick et al.

(10) Patent No.: US 7,955,832 B2
(45) Date of Patent: Jun. 7, 2011

(54) **COMPOSITION USEFUL FOR PROTEIN FRAGMENT COMPLEMENTATION ASSAYS (PCA) USING FRAGMENTS OF *E. COLI*/TEM-1 β-LACTAMASE**

(75) Inventors: Stephen William Watson Michnick, Montreal (CA); André Galarneau, Ste-Julie (CA)

(73) Assignee: ODYSSEY THERA Inc., San Ramon, CA (US)

( * ) Notice: Subject to any disclaimer, the term of this patent is extended or adjusted under 35 U.S.C. 154(b) by 628 days.

(21) Appl. No.: 11/002,259

(22) Filed: Dec. 3, 2004

(65) Prior Publication Data
US 2005/0233348 A1 Oct. 20, 2005

Related U.S. Application Data

(60) Division of application No. 09/870,018, filed on May 31, 2001, now Pat. No. 6,828,099, and a continuation-in-part of application No. 09/499,464, filed on Feb. 7, 2000, now Pat. No. 6,428,951, which is a continuation of application No. 09/017,412, filed on Feb. 2, 1998, now Pat. No. 6,270,964.

(60) Provisional application No. 60/208,485, filed on Jun. 2, 2000.

(51) Int. Cl.
*C12N 9/78* (2006.01)

(52) U.S. Cl. .................................................... 435/227
(58) Field of Classification Search .................. None
See application file for complete search history.

(56) References Cited

U.S. PATENT DOCUMENTS
2004/0038317 A1* 2/2004 Balint et al. ................... 435/7.2

OTHER PUBLICATIONS
John et al., Two Pairs of Oppositely Charged Amino Acidfsr om Jun and Fos Confer Heterodimerization to GCN4 Leucine Zipper, The Journal of Biological Chemistry Inc. vol. 269 No. 23, Issue of Jun. 10, pp. 16247-16253, 1994.*

* cited by examiner

*Primary Examiner* — Nashaat T Nashed
(74) *Attorney, Agent, or Firm* — Isaac A. Angres

(57) ABSTRACT

The present invention describes an assay method comprising: (A) generating (1) at least a first fragment of a reporter molecule linked to a first interacting domain and at least a second fragment of a reporter molecule linked to a second interacting domain, or (2) nucleic acid molecules that code for (A)(1) and subsequently allowing said nucleic acid molecules to produce their coded products; then, (B) allowing interaction of said domains; and (C) detecting reconstituted reporter molecule activity, where said reporter molecule can react with a penicillin- or a cephalosporin-class substrate.

5 Claims, 4 Drawing Sheets

- Family of enzymes that cleave penicillins and cephalosporins very efficiently
- A well characterised isoform is the 29 kD TEM-1 Beta-lactamase
  - 3D structure
  - Hydrolysis mechanism
  - Substrates and inhibitors
- Plasmid encoded ampicillin resistance gene from *E. coli*

FKBP/FRB Domain

FKBP/FRB Domain

SEQUENCE LISTING

<160> NUMBER OF SEQ ID NOS: 6

<210> SEQ ID NO 1
<211> LENGTH: 45
<212> TYPE: PRT
<213> ORGANISM: artificial sequence
<220> FEATURE:
<223> OTHER INFORMATION: synthetic

<400> SEQUENCE: 1

Gly Leu Tyr Gly Leu Tyr Gly Leu Tyr Gly Leu Tyr Ser Glu Arg Gly
1               5                   10                  15

Leu Tyr Gly Leu Tyr Gly Leu Tyr Gly Leu Tyr Ser Glu Arg Gly Leu
            20                  25                  30

Tyr Gly Leu Tyr Gly Leu Tyr Gly Leu Tyr Ser Glu Arg
        35                  40                  45

<210> SEQ ID NO 2
<211> LENGTH: 34
<212> TYPE: DNA
<213> ORGANISM: artificial sequence
<220> FEATURE:
<223> OTHER INFORMATION: synthetic

<400> SEQUENCE: 2
aaaaaaaagc ggccgcacac ccagaaacgc tggt                        34

<210> SEQ ID NO 3
<211> LENGTH: 30
<212> TYPE: DNA
<213> ORGANISM: artificial sequence
<220> FEATURE:
<223> OTHER INFORMATION: synthetic

<400> SEQUENCE: 3
aaactcgagt tagccagtta atagtttgcg                             30

<210> SEQ ID NO 4
<211> LENGTH: 36
<212> TYPE: DNA
<213> ORGANISM: artificial sequence
<220> FEATURE:
<223> OTHER INFORMATION: synthetic

<400> SEQUENCE: 4
aaaaaaaagc ggccgcacta cttactctag cttccc                      36

<210> SEQ ID NO 5
<211> LENGTH: 31
<212> TYPE: DNA
<213> ORGANISM: artificial sequence
<220> FEATURE:
<223> OTHER INFORMATION: synthetic

<400> SEQUENCE: 5
aaactcgagt taccaatgct taatcagtga g                           31

<210> SEQ ID NO 6
<211> LENGTH: 15
<212> TYPE: PRT
<213> ORGANISM: artificial sequence
<220> FEATURE:
<223> OTHER INFORMATION: synthetic

<400> SEQUENCE: 6

-continued

```
Gly Leu Tyr Gly Leu Tyr Gly Leu Tyr Gly Leu Tyr Ser Glu Arg
1               5               10              15
```

COMPOSITION USEFUL FOR PROTEIN FRAGMENT COMPLEMENTATION ASSAYS (PCA) USING FRAGMENTS OF E. COLI/TEM-1 β-LACTAMASE

This application is a divisional of application Ser. No. 09/870,018 filed May 31, 2001; now U.S. Pat. No. 6,828,099. This Application also claims the benefit of U.S. Provisional Application No. 60/208,485 filed Jun. 2, 2000, the entire contents of which are hereby incorporated by reference. This Application is also a continuation-in-part U.S. Ser. No. 09/499,464 filed Feb. 7, 2000; and now U.S. Pat. No. 6,428,951; which is a continuation of U.S. Ser. No. 09/017,412 filed Feb. 2, 1998; and now U.S. Pat. No. 6,270,964. The entire contents of all those patents and applications are incorporated by reference herein.

TECHNICAL FIELD OF THE INVENTION

The present invention relates generally to protein complementation assays (PCA) and more specifically to PCA assays based on the E. coli TEM-1 β-Lactamase for the detection of protein-protein, protein-small molecule and protein nucleic acid interactions.

BACKGROUND OF THE INVENTION

Applicants' have previously described oligomerization domain-assisted complementation of enzyme fragments as a general strategy for detecting protein-protein, protein small molecule and protein nucleic acid interactions (ref. 9). In the present invention, we describe assays based on the E. coli TEM-1 β-Lactamase (Accession number: AAB59737). In the present invention, applicants' disclose three assays in mammalian cells: (1), an in vitro colorimetric assay using the substrate nitrocefin, and (2) an in vivo positive/negative fluorescence assay using the substrate CCF2/AM. The invention is also directed to positive and negative survival assays using cephalosporin-cytotoxic pro-drug conjugates, as well as a series of β-lactamase point mutations that would be predicted to enhance the efficiency of the β-lactamase PCA.

The TEM-1 β-lactamase is a member of a family of bacterial enzymes that hydrolyze antibiotics of the penicillin and cephalosporin class, thus imparting resistance to bacteria expressing these enzymes. TEM-1 β-lactamase is the standard ampicillin resistance gene included in most plasmids used in molecular biology. The three-dimensional structure, proposed catalytic mechanism and optimal substrates and inhibitors have been well documented. TEM-1 β-Lactamase is a small (29 kiloDaltons) and monomeric protein consisting of 286 amino acids. The first 23 amino acids constitute a secretory signal peptide. β-lactamases catalyses the irreversible hydrolysis of the amide bond of β-lactam rings in penicillin or cephalosporin compounds. β-lactamases are secreted into the periplasmic space of gram-negative strains or into the outer media by their gram-positive counterparts where they normally act. However, they will accumulate in the cytoplasm when expressed in E. coli or other prokaryotic or eukaryotic cells if the secreting signal peptide is genetically deleted, without effecting catalytic activity.

TEM-1 β-lactamase meets all of the essential criteria to be an excellent candidate for a PCA strategy. Specifically, TEM-1 β-lactamase is a relatively small, monomeric protein and is well characterized both structurally and functionally. TEM-1 β-lactamase can be expressed in and is not toxic to prokaryotes and eukaryotes. In addition to these, unique features include that: First, β-Lactamase is strictly a bacterial enzyme and has been genetically deleted from many standard E. coli strains. It is not present at all in eukaryotes. Thus, a β-lactamase PCA could be used universally in eukaryotic cells and many prokaryotes, without any intrinsic background. Second, assays are based on catalytic turnover of substrates with rapid accumulation of product. This enzymatic amplification should allow for relatively weak molecular interactions to be observed. Finally, the assay can be performed simultaneously or serially in a number of modes, such as in vitro calorimetric or fluorometric assays, or in vivo fluorescence or survival assays. Assays can be performed independent of the measurement platform and can easily be adapted to high-throughput formats requiring only one pipetting step.

The PCA strategy of the present invention is based on the reassembly of two rationally designed complementary fragments of TEM-1 β-lactamase. Crystal structures of TEM-1 suggest that residues 196-200 form a loop situated outside of the core of the protein and distal to the enzymatic pocket (FIG. 1). This loop is not implicated in the catalytic machinery and seems not to be important for catalysis (ref. 4). For these reasons, this site was selected to generate the two fragments. We chose to cut in the middle of the loop between residues Glu197 and Leu198. In addition, the secreting signal peptide of 23 amino acids was deleted to leave only the functional enzyme. Thus fragment [1] (BLF[1]) consists of residues 24 to 197 and fragment [2] (BLF[2]) of residues 198-286. Each of these fragments are linked to interacting domains (GCN 4 leucine Zipper or the pair of rapamycin inducible interacting proteins FKBP/FRB domain) by a linker of 15 amino acids (Gly-Gly-Gly-Gly-Ser)$_3$ (SEQ. ID No. 1).

OBJECTS OF THE INVENTION

A primary object of the present invention are protein complementation assays (PCA) based on the E. coli TEM-1 β-Lactamase.

Another object of the present invention is an in vitro colorimetric PCA assay in mammalian cells using the substrate nitrocefin.

A further object of the invention is an in vivo positive/negative fluorescence PCA assay in mammalian cells using the substrate CCF2/AM.

Still, another object of the invention is positive and negative survival assays using cephalosporin-cytotoxic pro-drug conjugates.

An additional object of the invention is positive and negative survival assays using a series of β-lactamase point mutations that would be predicted to enhance the efficiency of the β-lactamase PCA.

We have found that these objects and others are achieved by the use of E. coli TEM-1 β-Lactamase as further described below.

SUMMARY OF THE INVENTION

Figure 1:
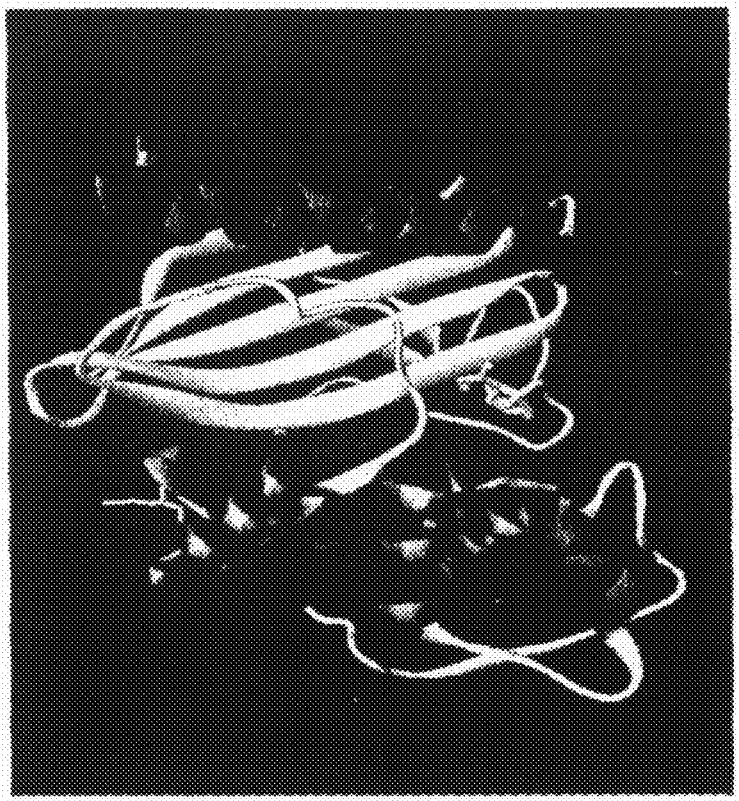
FIG. 1 illustrates technical information about the enzymes of the invention as well as the 3-D structure (ref. 7) of β-lactamase.

The instant invention is directed to an assay method comprising: (A) generating: (1) at least a first fragment of a reporter molecule linked to a first interacting domain and at least a second fragment of a reporter molecule linked to a second interacting domain, or (2) nucleic acid molecules that code for (A)(1) and subsequently allowing said nucleic acid molecules to produce their coded products; then, (B) allowing interaction of said domains; and (C) detecting reconstituted reporter molecule activity, where said reporter molecule can react with a penicillin- or cephalosporin-class substrate.

The invention is also directed to an assay method comprising: (A) exposing a host cell to: (1) at least a first fragment of a reporter molecule linked to a first interacting domain and at least a second fragment of a reporter molecule linked to a second interacting domain; or (2) compounds that code therefor; and (B) detecting reconstituted reporter molecule activity, where a reporter molecule and a host cell are used that yield a signal essentially without any intrinsic background.

In the present invention, there is also described an assay method comprising: (A) exposing a host cell to: (1) at least a first fragment of a reporter molecule linked to a first interacting domain and at least a second fragment of a reporter molecule linked to a second interacting domain; or (2) compounds that code therefor; and (B) detecting reconstituted reporter molecule activity, where a reporter molecule substrate is added that becomes trapped within said cell after entrance therein.

The invention is further directed to an assay method comprising: (A) exposing a host cell to: (1) at least a first fragment of a reporter molecule linked to a first interacting domain and at least a second fragment of a reporter molecule linked to a second interacting domain; or (2) compounds that code therefor; and (B) detecting reconstituted reporter molecule activity, where a reporter molecule substrate is added that has a fluorescent signal-producing system covalently associated therewith.

The present invention also describes an assay method comprising: (A) exposing a host cell to: (1) at least a first fragment of a reporter molecule linked to a first interacting domain and at least a second fragment of a reporter molecule linked to a second interacting domain; or (2) compounds that code therefor; and (B) detecting host cell survival as an indication of reconstituted reporter molecule activity.

In another embodiment, the invention discloses an assay method comprising: (A) exposing a host cell to: (1) at least a first fragment of a reporter molecule linked to a first interacting domain and at least a second fragment of a reporter molecule linked to a second interacting domain; or (2) compounds that code therefor; (B) further exposing said cell to a compound to be assayed for its ability to interfere with interaction of said first and second domains; and (C) detecting host cell survival as an indication of interference with said interaction.

The invention also teaches a composition comprising a compound which comprises a fragment of an interacting domain linked to a fragment of a reporter molecule that can hydrolyze either a penicillin class substrate or a cephalosporin class substrate.

In a further embodiment, the invention is directed to a composition comprising: (A) a first compound comprising a first fragment of an interacting domain linked to a first fragment of a reporter molecule that can hydrolyze either a penicillin class substrate or a cephalosporin class substrate; and (B) a second compound comprising a second fragment of an interacting domain linked to a second fragment said reporter molecule.

The instant invention also describes an assay method comprising: (A) allowing at least two molecules capable of mutual interaction to draw into close molecular proximity at least two reporter molecule fragments which, when in close molecular proximity, form a complex capable of reaction with a penicillin- or cephalosporin-class substrate; and (B) detecting a signal resulting from said reaction.

In a further embodiment, the invention describes an assay method comprising: (A) allowing at least two molecules capable of mutual interaction to draw into close molecular proximity at least two reporter molecule fragments which, when in close molecular proximity, form a complex capable of reaction with a penicillin- or cephalosporin-class substrate; and (B) detecting a signal resulting from said reaction, where there is essentially no intrinsic background in the assay.

The instant invention is also directed to an assay method comprising: (A) allowing at least two molecules capable of mutual interaction to draw into close molecular proximity at least two reporter molecule fragments which, when in close molecular proximity, form a complex capable of reaction with a penicillin- or cephalosporin-class substrate; and (B) detecting a signal resulting from said reaction, where said reaction occurs with a cell and said substrate becomes trapped within said cell after entrance therein.

The invention further describes an assay method comprising: (A) allowing at least two molecules capable of mutual interaction to draw into close molecular proximity at least two reporter molecule fragments which, when in close molecular proximity, form a complex capable of reaction with a penicillin- or cephalosporin-class substrate; and (B) detecting a signal resulting from said reaction, where a reporter molecule substrate is added that has a fluorescent signal-producing system covalently associated therewith.

The invention further provides a cellular assay method comprising: (A) allowing at least two molecules capable of mutual interaction to draw into close molecular proximity at least two reporter molecule fragments which, when in close molecular proximity, form a complex capable of reaction with a penicillin- or cephalosporin-class substrate; and (B) detecting cell survival as an indication of said reaction.

DESCRIPTION OF THE PREFERRED EMBODIMENTS

Substrates for Enzymatic Assay of β-Lactamase

Figure 2B:
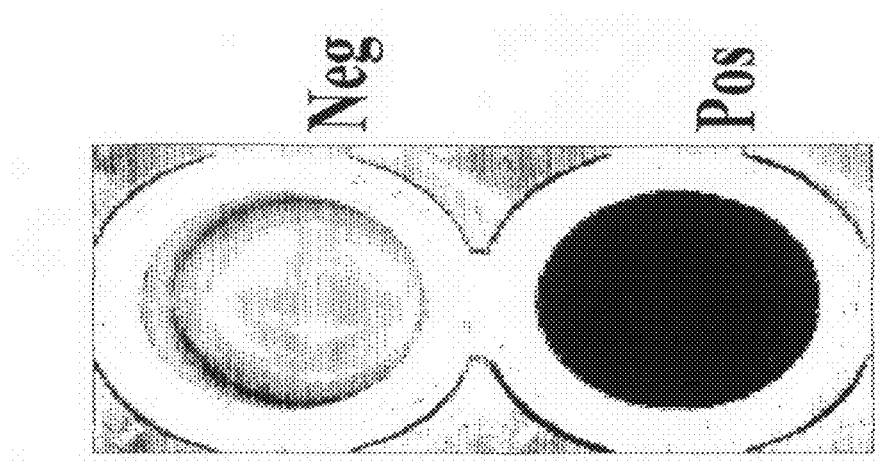
FIG. 2B describes the visualization of positive and negative controls wherein Negative: yellow substrate, red: hydrolyzed product of nitrocefin.
Figure 2A:
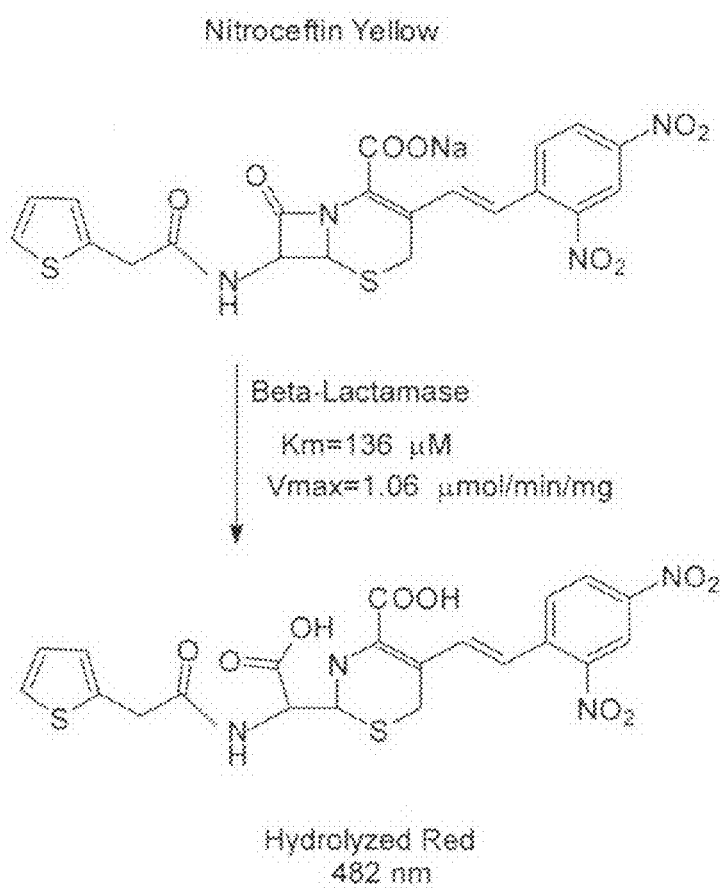
FIG. 2A shows the chemical structure of Nitrocefin and mechanism of hydrolysis of β-lactams.
Figure 3A:
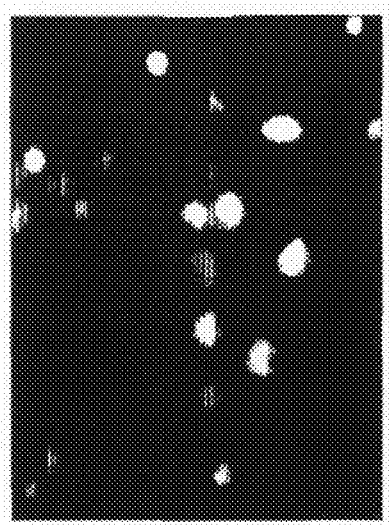
FIG. 3 illustrates GCN4 Zipper interactions in HEK 293 cells wherein (A) are untransfected cells, (B) are cells transfected with wild-type TEM-1 β-Lactamase, (C) is the Negative Control Cells transfected with non interacting pairs of protein FRB-5a.a.-BLF[1] and GCN4Zip-5a.a.-BLF[2], and (D) are the Positive Control Cells transfected with interacting pairs of protein GCN4Zip-5a.a.-BLF[1] and GCN4Zip-5a.a.-BLF[2].
Figure 3B:
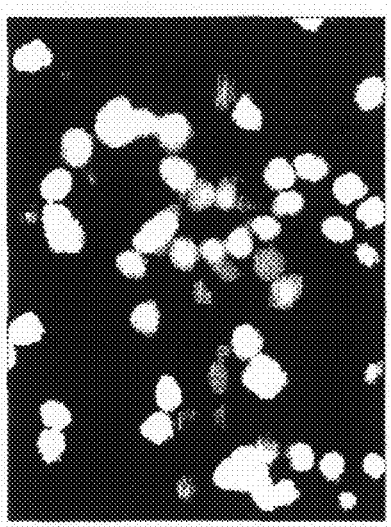
Figure 3C:
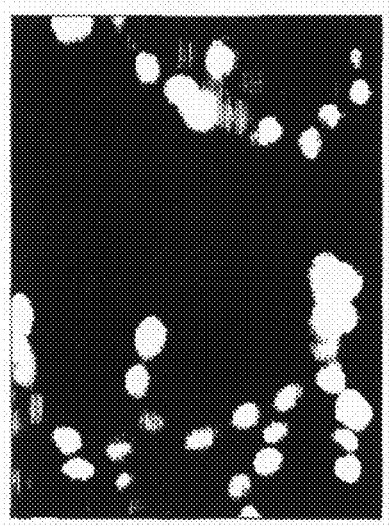
Figure 3D:
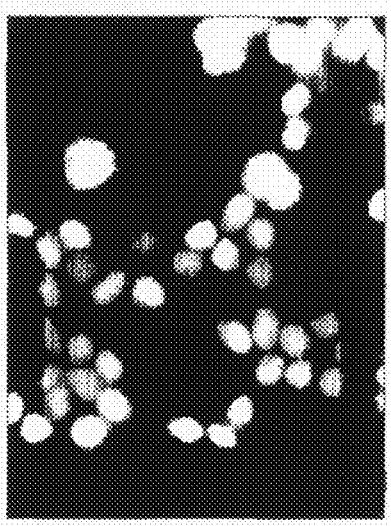

In practicing the instant invention two substrates have been used to study the β-lactamase PCA. The first one is the cephalosporin Nitrocefin. This substrate is used in the in vitro colorimetric assay. β-lactamase is quite efficient for this substrate, having a kcat/km of 17,000 mM$^{-1}$*s$^{-1}$ (ref. 4). Substrate conversion can be easily observed by eye; the substrate is yellow in solution while the product is a distinct ruby red color. The rate of hydrolysis can be monitored quantitatively with any spectrophotometer by measuring the appearance of red at 492 nm. Signal to background, depending on the mode of measurement can be greater than 30:1 (FIG. 2). As described below, this assay, at present is performed with whole cell lysates, as nitrocefin is not membrane permeant. However, in principle addition of ester groups could be sufficient to allow for membrane permeability and a true in vivo colorimetric assay could be performed.

We also performed an in vivo fluorometric assay using the substrate CCF2/AM. While not as good a substrate as nitrocefin (kcat/km of 1260 mM$^{-1}$*s$^{-1}$) CCF2/AM has unique features that make it a useful reagent for in vivo PCA. First, CCF2/AM contains butyryl, acetyl and acetoxymethyl esters, allowing diffusion across the plasma membrane where cytoplasmic esterases catalyze the hydrolysis of its ester functionality releasing the polyanionic (4 anions) β-lactamase substrate CCF2. Because of the negative charge of CCF2, the substrate becomes trapped in the cell. In the intact substrate fluorescence resonance energy transfer (FRET) can occur between a coumarin donor and fluorescein acceptor pair covalently linked to the cephalosporin core. The coumarin donor can be excited at 409 nm with emission at 447 nm which is within the excitation envelope of the fluorescence acceptor (maximum around 485 nm) leading to remission of green fluorescence at 535 nm. When β-lactamase catalyzes hydrolysis of the substrate the fluorescein moiety is eliminated as a free thiol. Excitation of the coumarin donor at 409 nm then emits blue fluorescence at 447 nm whereas the acceptor (fluorescein) is quenched by the free thiol.

Figure 4A:
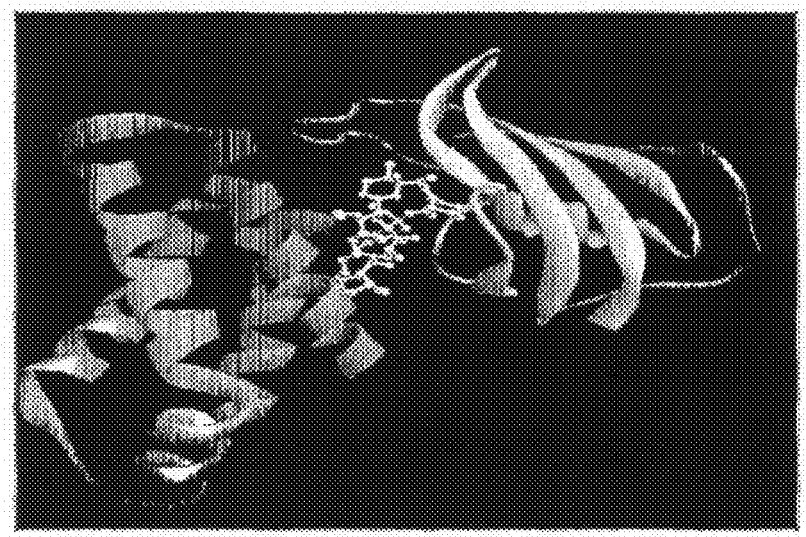
FIG. 4 describes FKBP and FRB interactions in HEK 293 cells wherein (A) is the structure of the interacting pair of FKBP and FRB domain induced by rapamycin, (B) is the quantitation of the dose-response induced interaction of FRB-5a.a.-BLF[1] and FKBP-5a.a.-BLF[2] with rapamycin concentration ranging from 0.15 nM to 0.3 µM. Inhibition of the FKBP/FRB domain interaction with FK506 concentration ranging from 6.9 nM to 15 µM against 50 nM rapamycin, (C) is the dose response induced interaction curve with rapamycin concentration ranging from 0.15 nM to 0.3 µM (Determined $K_d$ of 3 nM), and (D) is the inhibition curve of 50 nM rapamycin induced interaction between FKBP/FRB domain with FK506 concentration ranging from 6.9 nM to 15 µM.
Figure 4B:
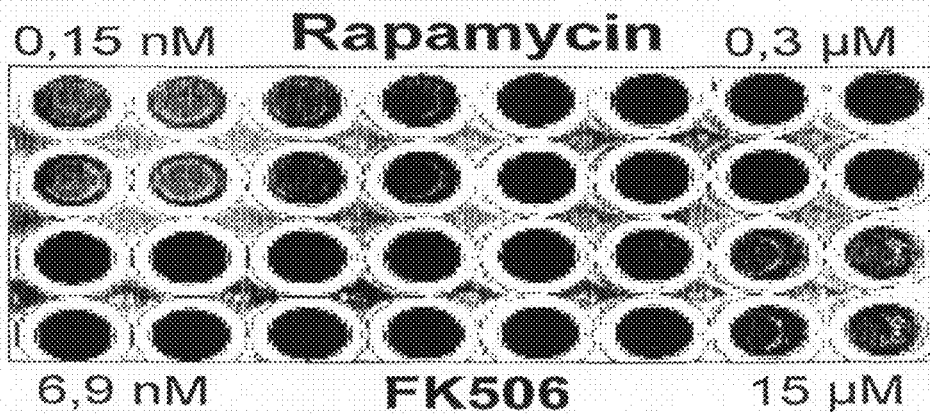

One can perform both positive and negative detection of protein-protein interactions using the CCF2/AM substrate. For example, positive detection for a protein-protein interaction consists in observing in cells, the conversion of green to blue fluorescence, whereas disruption of an interaction, a reversion to green fluorescence. This is illustrated by the rapamycin-induced FKBP FRB interaction (FIG. 4). The competitive inhibitor, FK506, disrupts the interaction of the FKBP-rapamycin-FRB interaction. While shown as a FK506 concentration-dependent reduction in blue fluorescence, equally it could be read as an augmentation of green fluorescence.

The invention is illustrated by the following non-limiting examples.

EXAMPLES

Example 1

Materials and Methods

DNA Constructs
GCN4 Zipper Dimerization System.

Fragments of β-lactamase (F[1] and F[2]) were amplified by PCR using Progene (Mendel Scientific) from the ampicillin resistance gene of the vector pQE-32 (Qiagen) with the following oligos: BLF[1] forward: AAAAAAAAGCGG-CCGCACACCCAGAAACGCTGGT (SEQ. ID. No. 2); BLF[1] reverse: AAACTCGAGTTA-GCCAGTTAAT-AGTTTGCG (SEQ. ID. No. 3); BLF[2] forward: AAAAAAAAGCGGCCGCACTAC-TTACTCTAGCT-TCCC (SEQ. ID. No. 4); BLF[2] reverse: AAACTCGAGT-TACCAATGCTTAAT-CAGTGAG (SEQ. ID. No. 5). The PCR products were introduced at the 3' end of a flexible linker of five amino acids (Gly-Gly-Gly-Gly-Ser) (SEQ. ID. No. 6) in a previously described construct consisting of GCN4 leucine zipper-5 a.a. in pMT3 vector (a eukaryotic expression vector) resulting in the following constructs: Zip-5a.a.-BLF[1] and Zip-5a.a.-BLF[2] with a five amino acids linker.

Example 2

FKBP and FRB Dimerization System

The PCR product were introduced at the 3' end of a flexible linker of five amino acids (Gly-Gly-Gly-Gly-Ser) (SEQ. ID. No. 6) in a previously described construct consisting of FRB (FKBP-rapamycin binding domain of FRAP; FRAP is the FKBP-rapamycin binding protein)-5a.a. and FKBP(the FK506 binding protein)-5a.a. in pMT3 vector (ref 10) resulting in the constructs FRB-5a.a.-BLF[1] and FKBP-5a.a.-BLF[2] respectively. BLF[1] and BLF[2] correspond respectively to residues 23-197 and 198-286 of TEM-1 β-lactamase.)

Example 3

Cell Culture and Transfection

HEK 293 T cells were split 24 h before transfection at 1×10$^5$ in 12-well plates in DMEM (Life Technologies; Grand Island, N.Y.) which was enriched with 10% cosmic calf serum (HyClone). Cells were transfected with the different constructs by using Fugene reagent (Roche) according to the manufacturer's instructions.

Example 4

In Vitro Enzymatic Assay with Nitrocefin 48 h after transfection, cells were washed 3 times with cold Phosphate Buffered Saline (PBS) resuspended in 300 μl of cold PBS and kept on ice. Cells were then centrifuged at 4° C. for 30 seconds, the supernatant discarded and cells resuspended in 100 μl of cold Phosphate buffer 100 mM pH 7.4 (β-lactamase reaction buffer). Cells were lysed with 3 cycles of freeze and thaw by freezing in dry ice/ethanol for 10 minutes and thawing in a water bath at 37° C. for 10 minutes. Cell membrane and debris were removed by centrifugation at 4° C. for 5 minutes (10,000×g). The supernatant whole cell lysate was then collected and stored at −20° C. until assays were performed. Assays were performed in 96-well plates (Corning Costar, Cat. no: 3595). For testing β-lactamase activity, 100 μl of Phosphate buffer 100 mM pH 7.4 was aliquoted into each well. To this was added 78 μl of H$_2$O and 2 μl of Nitrocefin 10 mM (final concentration of 100 μM). Finally, 20 μl of unfrozen cell lysate was added (final buffer concentration of 60 mM; final nitrocefin concentration 60 μM). The assays were performed with a Perkin-Elmer HTS 7000 Series Bio Assay Reader in absorption mode with the following settings:

A—Measurement mode: Absorption
B—Measurement filter: 492 nm
C—Shaking time: 5 sec
D—Shaking mode: Orbital
E—Shaking intensity: Low
F—Number of flashes: 3
G—Integration start: 0 μs
H—Integration time: 40 μs I—Number of measurements: 61
J—Length of measurement: 00:20:00
K—Measurement interval: 00:00:20

Example 5

In Vivo Enzymatic Assay and Fluorescent Microscopy with CCF2/AM

HEK 293 cells were cotransfected as described above, and plated onto 6 well plates for suspension assays or onto 15 mm glass coverslips (Ted Pella Inc.) for fluorescence microscopy. 24 h after transfection, cells are split again to assure 50% confluency the following day (cell density of $1.5 \times 10^5$). 24 h after splitting the cells were washed 3 times with PBS to remove all traces of serum. Cells were then loaded with the following: 1 µM of CCF2/AM (diluted from a stock 1 mM solution in DMSO) diluted into a physiologic saline solution (HEPES, 10 mM; Sucrose, 6 mM; Glucose, 10 mM; NaCl, 140 mM; KCl, 5 mM; $MgCl_2$, 2 mM; $CaCl_2$, 2 mM; pH 7.35) for 1 hour. Cells were then washed twice with the physiologic saline. The cells were resuspended into the same solution and $1 \times 10^6$ cells were aliquoted into a 96-well fluorescence white plate (Dynex no 7905, VWR Scientific, Cat. no: 62402-980) were read for blue fluorescence with a Perkin Elmer HTS 7000 Series Bio Assay Reader with the following settings:
A. Measurement mode: Fluorescence [RFU] Top
B. Excitation filter: 405 nM
C. Emission filter: 465 nM
D. Gain mode: Manual
E. Gain: 60
A. Number of flashes: 3
B. Lag time: 0 µs
A. Integration time: 40 µs
B. Shaking time: 5 sec
C. Shaking mode: Orbital
D. Shaking intensity: Low For fluorescence microscopic studies the cells were kept in the physiologic saline on the 15 mm glass coverslips. Treatment of cells prior to microscopy was the same as described above unless otherwise indicated. Fluorescence microscopy was performed on live HEK 293 T cells with an inverse Nikon Eclipse TE-200 (objective plan fluor 40× dry, numerically open at 0.75) Images were taken with a digital CCD cooled (−50° C.) camera, model Orca-II (Hamamatsu Photonics (expositions for 1 second, binning of 2×2 and digitalization 14 bits at 1.25 MHz). Source of light is a Xenon lamp Model DG4 (Sutter Instruments). Emission filters can be change by a emission filter switcher (model Quantoscope) (Stranford Photonics). Images were visualized with ISee software (Inovision Corporation) on a O2 Silicon Graphics computer. The following selected filters were used:

| The filters used: | Filter set #31016 (Chroma Technologies); |
|---|---|
| Excitation filter: | 405 nm (passing band of 20 nm); |
| Dichroic Mirror: | 425 nm DCLP; |
| Emission filter #1: | 460 nm (passing band of 50 nm); |
| Emission filter #2: | 515 nm (passing band of 20 nm). |

Example 6

Improving the β-Lactamase PCA

Mutational Studies of the Fragments

Several point mutations in full length TEM-1 β-lactamase are known to improve catalytic activity. These mutations are E104K and M182T for BLF[1] and G238S for BLF[2]. For example, the minimum inhibitory concentration for cefotaxime is 20,000 fold higher than the wild-type TEM-1 and catalytic efficiency ($k_{cat}/k_m$) is 2383 times higher. Two of these mutations are located in fragment [1] and the other in fragment [2].

Example 7

Positive and Negative Survival Selection Assays

As mentioned in the introduction, TEM-1 β-lactamase is a standard antibiotic resistance gene incorporated into most commercial vectors for clonal positive selection. It is obvious then, that a PCA can be designed based on the same principal, where positive selection for reassembly of the enzyme by interaction of proteins fused to the fragments would be the basis for survival-selection. The same fragments as used in the mammalian assays can be used, while in both cases, the 23 amino acid signal peptide sequence would need to be fused at the N-termini of both protein-BLF fusions.

The use of antitumor prodrugs forms the basis for a negative selection assay in bacteria or mammalian cells[12]. The chemistry used in the CCF2/AM strategy has been previously applied to designing cell-specific targeted antitumor agents. As in CCF2/AM a cytotoxic drug is conjugated to cephalosporin via a thioether, or other appropriate leaving group. Cells are then treated with a cell-surface antigen-specific antibody fused to β-lactamases. On encountering β-lactamase, the rearrangement about the cephalosporin β-lactam ring results in release of the cytotoxic prodrug in an active form. In a realization of a negative selection assay, the disruption of the interaction between two proteins that are fused to the β-lactamase fragments would render cells expressing these fusions resistant to treatment with the cytotoxic prodrugs by the prevention of fragment complementation and thus β-lactamase activity. This approach could be used to screen for compounds that inhibit a protein-protein interaction.

REFERENCES CITED

1. Christensen, H., Martin, M. T. & Waley, S. G. (1990), Biochem. J. 266, 853.
2. Sutcliffe, J. G. (1978), PNAS 75, 3737.
3. Page, M. I. (1987), Adv. Phys. Org. Chem. 23, 165.
4. Matagne, A., Lamotte-Brasseur, J. & Frere, J. M. (1998), Biochem. J. 330, 581.
5. Philippon, A., Dusart, J. Joris, B. & Frere, J. M. (1998), CMLS 54, 341.
6. Kadonaga, J. T. et al. (1984), J. Biol. Chem. 259, 2149.
7. PDB Structure #: 1TEM or 1AXB
8. O'Callaghan et al. (1972)
9. Zlogarnik, G. et al. (1998), Science 279, 84.
10. Remy, I. & Michnick S. (1999), PNAS 96, 5394.
11. Zaccolo, M. & Gherardi, E. (1999), J. Mol. Biol. 285, 775.
12. Kerr, D. E., Li, Z., Siemers, N. O., Senter, P. D. & Vrudhula, V. M., 1998. Development and activities of a new melphalan prodrug designed for tumor-selective activation. *Bioconjug Chem* 9: 255-259; Vrudhula, V. M., Svensson, H. P. & Senter, P. D., 1995. *J Med Chem* 38: 1380-1385; Senter, P. D., Svensson, H. P., Schreiber, G. J., Rodriguez, J. L. & Vrudhula, V. M., 1995. *Bioconjug Chem* 6: 389-394; Svensson, H. P., Wallace, P. M. & Senter, P. D., 1994. *Bioconjug Chem* 5: 262-267.

Although the present invention has been described with reference to specific details of certain embodiments thereof, it is not intended that such detail should be regarded as limitations upon the scope of the invention, except as and to the extent that they are included in the accompanying claims.

What is claimed is:

1. A composition comprising:
   (A) a first compound comprising a first fragment of an interacting domain linked to a first fragment of a β-lactamase reporter enzyme that catalyses the hydrolysis of the amide bond of β-lactam rings in penicillin or cephalosporin compounds; and
   (B) a second compound comprising a second fragment of an interacting domain linked to a second fragment of said β-lactamase reporter enzyme wherein components (A) and (B) upon complementation results in reconstitution of β-lactamase activity.

2. A composition comprising a compound which comprises a fragment of an interacting domain linked to a first fragment of a β-lactamase reporter enzyme that catalyses the hydrolysis of the amide bond of β-lactam rings in penicillin or cephalosporin compounds upon binding to a second complementary fragment of the β-lactamase reporter enzyme.

3. A composition according to claim 2 or 1 where said interacting domain is derived from a leucine zipper or from a rapamycin-inducible interacting protein.

4. A composition according to claim 2 or 1 where said interacting domain is derived from a GCN 4 leucine zipper or from FKBP/FRB.

5. A composition according to claim 2 or 1 wherein at least one of said compounds has a flexible linker joining its reporter molecule fragment to its associated interacting domain.

* * * * *